United States Patent [19]

Henrick

[11] 4,226,872

[45] Oct. 7, 1980

[54] PYRIDYL ESTERS OF α-SUBSTITUTED AMINO ACIDS

[75] Inventor: Clive A. Henrick, Palo Alto, Calif.

[73] Assignee: Zoecon Corporation, Palo Alto, Calif.

[21] Appl. No.: 69,445

[22] Filed: Aug. 24, 1979

Related U.S. Application Data

[63] Continuation-in-part of Ser. No. 16,775, Mar. 2, 1979, abandoned.

[51] Int. Cl.² .................. A01N 9/22; C07D 213/55
[52] U.S. Cl. .................................. 424/263; 546/270; 546/291; 546/301; 546/302
[58] Field of Search ............... 546/291, 302, 301, 270; 424/263

[56] References Cited

U.S. PATENT DOCUMENTS 4,163,787  8/1979  Malhotra ............................. 546/270

*Primary Examiner*—Alan L. Rotman

[57] ABSTRACT

Pyridyl esters and thiolesters of amino acids, intermediates therefor, snythesis thereof and the use of said esters and thiolesters and compositions for the control of pests.

32 Claims, No Drawings

PYRIDYL ESTERS OF α-SUBSTITUTED AMINO ACIDS

This is a continuation-in-part of Ser. No. 016,775, filed March 2, 1979, now abandoned, the entire disclosure of which is incorporated herein by reference.

This invention relates to novel esters and thiolesters of α-substituted amino acids, novel intermediates therefor, synthesis thereof, and the control of pests.

The esters and thiolesters of the present invention are represented by the following formula (A):

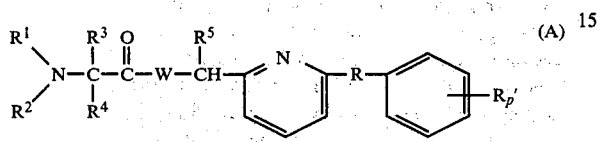

wherein,

R is oxygen, sulfur, methylene or carbonyl;

R' is fluoro, bromo, chloro, trifluoromethyl, methyl, methoxy or methylthio;

p is zero, one or two; W is oxygen or sulfur;

$R^1$ is cycloalkyl, cycloalkenyl, cycloalkenyl substituted with halo or lower alkyl, or the group

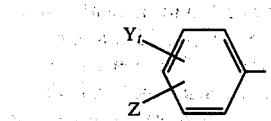

in which t is zero, one, two, three or four; Y is independently selected from hydrogen, lower alkyl, lower haloalkyl, lower alkoxy, lower alkylthio, lower alkylcarbonyl, lower alkoxycarbonyl, lower acyloxy, halogen, cyano, nitro, and lower haloalkylthio; and Z is independently selected from the values of Y, cycloalkyl, and lower haloalkoxy; or Y and Z form a methylenedioxy group;

$R^2$ is hydrogen, lower alkyl, lower haloalkylcarbonyl, or formyl; $R^3$ is lower alkyl of 2 to 5 carbon atoms, lower alkenyl of 2 to 5 carbon atoms, lower haloalkyl of 1 to 4 carbon atoms, lower haloalkenyl of 2 to 4 carbon atoms, or lower cycloalkyl of 3 or 4 carbon atoms; $R^4$ is hydrogen or fluoro; $R^5$ is hydrogen, cyano, ethynyl, methyl, ethyl, trifluoromethyl or thioamide; and the salt thereof of a strong inorganic acid or organic acid.

The compounds of the present invention represented by formula (A) are useful agents for the control of pests such as insects and acarids.

In the description hereinafter and the appended claims, each of R through $R^5$, W, Y, Z, p and t is as defined hereinabove, unless otherwise specified.

The compound of formula (A) can be synthesized as outlined below.

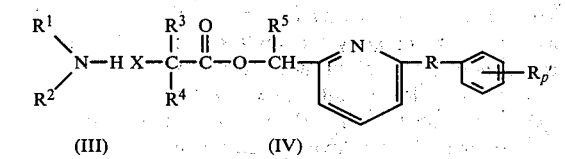

In the general practice of the above synthesis, an acid, salt thereof or the acid chloride is reacted with an alcohol of formula II to form the carboxylic ester A'. For example, an acid chloride of the acid of formula I is reacted with an alcohol of formula II in an organic solvent such as diethyl ether in the presence of triethylamine. In another embodiment, an acid of formula I and an alcohol of formula II are reacted in an organic solvent such as methylene chloride in the presence of 4-dimethylaminopyridine and dicyclohexylcarbodiimide to form an ester of formula A'. In another embodiment, the esters of formula A' are synthesized by reaction of an acid of formula I with phosgene in the presence of an ether such as 1,4-dioxane to form the corresponding oxazolidine-2,5-dione, which is then reacted with an alcohol of formula II to make the corresponding ester of formula A'. In another synthesis, the acid of formula I or salt thereof is reacted with the bromide, chloride or mesylate of the alcohol for formula II to form an ester of formula A'. The starting materials of formula I are described by Henrick and Garcia, Offenlegungsschrift No. 28 12 169. The alcohols of formula II can be made as described by Malhotra and Ricks, Offenlegungsschrift No. 28 10 881 and Maeda and Hirose, CA 81 135964k and 80 59873s and references cited therein.

In another embodiment, the compounds of formula (A) can be prepared by the reaction of an amine (III) with an α-halo ester of formula IV (X is bromo or chloro).

The reaction of an amine (III) and halo ester (IV) is generally carried out neat or in an organic solvent such as hexamethylphosphorictriamide, tetrahydrofuran, dimethylformamide, dimethylsulfoxide, or the like. The halo esters of formula IV can be prepared by reaction of an acid halide thereof with an alcohol of formula II.

The thiolesters of formula (A) can be prepared by reaction of, for example, the sodium salt of a thioacid corresponding to formula I with the bromide or mesylate of the alcohol of formula II.

The following terms wherever used in the description herein and the appended claims, have the meaning defined below, unless otherwise specified hereinafter.

The term "lower alkyl" refers to an alkyl group, straight or branched, having a chain length of one to eight carbon atoms. The term "lower haloalkyl" refers to an alkyl group substituted with one to three halogen atoms such as chloromethyl, fluoromethyl, trifluoromethyl, 2,2,2-trifluoroethyl, 6-chlorohexyl, 2-fluoroethyl, and the like. The term "lower alkoxy" refers to an alkoxy group, straight or branched, having a chain length of one to eight carbon atoms. The term "lower alkylthio" refers to an alkylthio group, straight or branched, having a chain length of one to eight carbon atoms.

The term "lower alkenyl" refers to an ethylenically unsaturated hydrocarbon group, straight or branched, having a chain length of two to eight carbon atoms and one or two ethylenic bonds such as vinyl, allyl, 3-butenyl, 2-hexenyl, i-propenyl, 2,4-hexadienyl, and the like. The term "lower haloalkenyl" refers to a lower alkenyl group substituted with one to three halogen atoms. The term "lower alkenyloxy" refers to an alkenyloxy group, straight or branched, of two to eight carbon atoms. The term "lower haloalkenyloxy" refers to a lower alkenyloxy group substituted with one to three halogen atoms.

The term "lower alkynyl" refers to an alkynyl group, straight or branched, having a chain length of two to eight carbon atoms and one or two acetylenic bonds. The term "lower haloalkynyl" refers to a lower alkynyl group having one to three halogen atoms. The term "lower alkynyloxy" refers to an alkynyloxy group, straight or branched, of three to eight carbon atoms.

The term "cycloalkyl" refers to a cycloalkyl group of three to eight cyclic carbon atoms. The term "cycloalkalkyl" refers to a cycloalkyl group wherein one hydrogen atom is replaced by a lower alkyl group, the total number of carbon atoms being from four to twelve, such as cyclopropanemethyl, cyclobutaneethyl, cyclohexanemethyl, and the like.

The term "aryl" refers to the aryl group phenyl or naphthyl. The term "aralkyl" refers to a lower alkyl group in which a hydrogen atom of the alkyl group is substituted by an aryl group, the total number of carbon atoms being from seven to twelve, such as benzyl, phenethyl, and the like. The terms "substituted aryl" and "substituted aralkyl" refer to an aryl group and an aralkyl group, respectively, substituted at one, two or three of the ring carbon atoms with a group selected from lower alkyl, lower haloalkyl, lower alkoxy, lower alkenyl, lower haloalkenyl, lower alkenyloxy, halogen, nitro, cyano, lower alkylthio, and the like.

The term "lower haloalkoxy" refers to a lower alkoxy group substituted with one to three halogen atoms.

The term "lower acyloxy" refers to a lower organic acyloxy group of one to six carbon atoms, such as acetoxy.

The compounds of the present invention of formula (A) have one or more asymmetric carbon atoms. The present invention includes each of the optical isomers and racemic mixtures thereof. In the examples hereinafter, unless otherwise specified, the compound prepared is a racemic mixture.

Included within the present invention are salts of the compounds of formula A. The salts are formed from strong inorganic acids or organic acids such as hydrochloric acid, sulfuric acid, phosphoric acid, p-toluenesulfonic acid, p-benzenesulfonic acid, methanesulfonic acid, Lewis acid and the like. Many of the compounds of formula A are oils which advantageously are converted into the salt for convenience of handling and formulating and superior stability. The salts are useful for the control of pests in the same way as the compounds of formula A.

The compounds of the present invention of formula A are useful pest control agents, particularly for the control of insects and acarids. In the use of the compounds of formula A for combating insects and acarids for the protection of agricultural crops, for example soybeans, cotton, alfalfa, etc., a compound of formula A, or mixtures thereof, together with a carrier is applied to the locus in a pesticidally effective amount. The carrier can be liquid or solid and include adjuvants such as wetting agents, dispersing agents and other surface active agents. The compounds of formula A can be used in formulations such as wettable powders, solutions, dusts, granules, emulsifiable concentrates, and the like. Suitable solid carriers include natural and synthetic silicates and clays, carbon or charcoal granules, natural and synthetic resins, waxes, and the like. Suitable liquid carriers include water, aromatic hydrocarbons, alcohols, vegetable and mineral oils, ketones, and the like. The amount of a compound of formula A in the formulation can vary widely, generally within the range of about 0.01 percent to about 90.0 percent, by weight.

As shown hereinafter, the compounds of the present invention are effective on many different insects and on acarids. The compounds are effective control agents for insects such as mosquitoes, flies, aphids, weevils and acarids such as the spider mite and ticks. Depending upon the particular combination of the substituents of formula A herein, the compounds have a broad or relatively narrow spectrum of unusually high pesticidal activity on insects and acarids. Among the pests against which the compounds of the present invention are pesticidally effective are insects of the order Lepidoptera, Orthoptera, Heteroptera, Homoptera, Diptera, Coleoptera or Hymenoptera, and acarids of the order Acarina including mites of the family Tetranychidae or Tarsonemidae and ticks such as Ornithodoros.

The compounds of the present invention can be used in combination with other pesticides such as the carbamates, phosphates and insect growth regulators, e.g. propoxur, carbaryl, naled, dichlorvos, methoprene, kinoprene, hydroprene, cyhexatin and resmethrin.

The following examples are provided to illustrate the practice of the present invention. Temperature is given in degrees Centigrade. RT means room temperature.

EXAMPLE 1

To a stirred solution of (6-phenoxy-2-pyridyl)methanol (0.2 g, 0.99 mmol) and triethylamine (0.14 g, 1.38 mmol) in ether (about 15 ml), under nitrogen, is added by syringe a solution of the acid chloride of N-(2-chloro-4-trifluoromethylphenyl)valine (1.5 mmol) in ether. The mixture is stirred for 30 minutes and then quenched with saturated aqueous sodium bicarbonate. The ether phase is washed with aqueous sodium bicarbonate, water and brine and filtered through silica. Evaporation of solvent, followed by thin layer chromatography using a circular chromatograph, eluting with 20% ether/hexane, gives the (6-phenoxy-2-pyridyl)methyl ester of N-(2-chloro-4-trifluoromethylphenyl)valine, a substantially colorless viscous oil.

The acid chloride is prepared by the reaction of N-(2-chloro-4-trifluoromethylphenyl)valine with phosgene in ether in the presence of a small amount of dimethylformamide.

EXAMPLE 2

A. To a solution of 6-phenoxypyridyl-2-carboxaldehyde (0.37 g, 1.8 mmol) in 25 ml of ether is added 25 ml of water followed by sodium cyanide (0.149 g, 3.04 mmol). The mixture is stirred vigorously while a solution of sodium bisulfite (0.257 g, 2.47 mmol) in 15 ml of water is added over about 5 minutes. The reaction mixture is stirred for two hours. The organic phase is separated, washed with water, dried over calcium sulfate and solvent evaporated to give cyano(6-phenoxy-2-pyridyl)methanol.

B. To the acid chloride of N-(2-fluoro-4-trifluoromethylphenyl)valine (2.5 mmol) in ether is added 1.3 ml of triethylamine followed by the cyano(6-phenoxy-2-pyridyl)methanol in 5 ml of ether, from part A above, over about 2 minutes. The reaction mixture is stirred for about 18 hours and then quenched with saturated aqueous sodium bicarbonate. The organic phase is washed with aqueous sodium bicarbonate, water and brine, dried over calcium sulfate and solvent evaporated. The crude product is chromatographed on a circular chromatograph eluting with 20% ether/hexane to give cyano(6-phenoxy-2-pyridyl)methyl ester of N-(2-fluoro-4-trifluoromethylphenyl)valine, pale yellow viscous liquid.

EXAMPLE 3

To a stirred solution of cyano(6-phenoxy-2-pyridyl)methanol (410 mg, 1.8 mmol), N-(2-chloro-4-trifluoromethylphenyl)valine (590 mg, 2.0 mmol) and dimethylaminopyridine (0.65 mmol) in 20 ml of methylene chloride and 2 ml of dimethylformamide is added N,N'-dicyclohexylcarbodiimide (2.0 mmol). The reaction mixture is stirred, under nitrogen, for two hours and then filtered and extracted with water. The aqueous phase is extracted with ether. The combined organic phases are washed with saturated aqueous sodium bicarbonate, water and saturated aqueous sodium chloride, dried over calcium sulfate and solvent evaporated. The crude product is chromatographed on a rotary chromatograph eluting with 25% ether/hexane to yield the cyano(6-phenoxy-2-pyridyl) methyl ester of N-(2-chloro-4-trifluoromethylphenyl)valine, a colorless, viscous liquid.

EXAMPLE 4

To a solution of 3-(4-chlorophenyl)-4-isopropyloxazolidine-2,5-dione (336 mg, 1.32 mmol) and dimethylaminopyridine in 5 ml of dry tetrahydrofuran is added a solution of (6-phenoxy-2-pyridyl)methanol (254 mg, 1.26 mmol) in 3 ml of dry tetrahydrofuran. The reaction mixture is stirred for about 20 hours, under dry air, and then diluted with ether followed by washing with saturated aqueous sodium bicarbonate, water and saturated aqueous sodium chloride. After drying over calcium sulfate, solvent is evaporated. The crude product, yellow liquid, is chromatographed on a rotary chromatograph eluting with 15% ether/hexane to give the (6-phenoxy-2-pyridyl)methyl ester of N-(4-chlorophenyl)valine, a colorless oil.

Following the above procedure, 3-(4-methylphenyl)-4-isopropyloxazolidine-2,5-dione is reacted with (6-phenoxy-2-pyridyl)methanol to give the (6-phenoxy-2-pyridyl)methyl ester of N-(4-methylphenyl)valine.

In the same way, 3-(4-trifluoromethylphenyl)-4-isopropyloxazolidine-2,5-dione is reacted with (6-phenoxy-2-pyridyl)methanol to give the (6-phenoxy-2-pyridyl)methyl ester of N-(4-trifluoromethylphenyl)valine.

EXAMPLE 5

Using the procedure of Example 3, each of the acids, N-(4-chloro-2-fluorophenyl)valine, N-(3-fluoro-4-methylphenyl)valine, N-(2-fluoro-4-methylphenyl)valine, N-(2,4-dichlorophenyl)valine, N-(4-bromo-2-fluorophenyl)valine, N-(4-trifluoromethylphenyl)valine, N-(2-chloro-4-methylphenyl)valine, and N-(2-methyl-4-trifluoromethylphenyl)valine is reacted with cyano(6-phenoxy-2-pyridyl)methanol to yield the respective ester:

cyano(6-phenoxy-2-pyridyl)methyl ester of N-(4-chloro-2-fluorophenyl)valine cyano(6-phenoxy-2-pyridyl)methyl ester of N-(3-fluoro-4-methylphenyl)valine cyano(6-phenoxy-2-pyridyl)methyl ester of N-(2-fluoro-4-methylphenyl)valine cyano(6-phenoxy-2-pyridyl)methyl ester of N-(2,4-dichlorophenyl)valine cyano(6-phenoxy-2-pyridyl)methyl ester of N-(4-bromo-2-fluorophenyl)valine cyano(6-phenoxy-2-pyridyl)methyl ester of N-(4-trifluoromethylphenyl)valine cyano(6-phenoxy-2-pyridyl)methyl ester of N-(2-chloro-4-methylphenyl)valine cyano(6-phenoxy-2-pyridyl)methyl ester of N-(2-methyl-4-trifluoromethylphenyl)valine

EXAMPLE 6

The acid N-(4-fluorophenyl)valine [2-(4-fluorophenylamino)-3-methylbutanoic acid] is reacted with cyano(6-phenoxy-2-pyridyl)methanol using the procedure of Example 3 to give the cyano(6-phenoxy-2-pyridyl)methyl ester of N-(4-fluorophenyl)valine [cyano(6-phenoxy-2-pyridyl)methyl 2-(4-fluorophenylamino)-3-methylbutanoate].

In the same way, using the procedure of Example 3, each of the acids under col. I is converted to the ester under col. II by reaction with cyano(6-phenoxy-2-pyridyl)methanol.

I 2-(4-methylphenylamino)-3-methylbutanoic acid
2-(4-chlorophenylamino)-3-methylbutanoic acid
2-(4-methoxyphenylamino)-3-methylbutanoic acid
2-(4-bromophenylmaino)-3-methylbutanoic acid
2-(t-butylphenylamino)-3-methylbutanoic acid
2-(4-ethylphenylamino)-3-methylbutanoic acid
2-phenylamino-3-methylbutanoic acid
2-(4-methylthiophenylamino)-3-methylbutanoic acid
2-(4-cyclopropylphenylamino)-3-methylbutanoic acid
2-(4-isopropylphenylamino)-3-methylbutanoic acid
2-(3-fluorophenylamino)-3-methylbutanoic acid
2-(2-methylphenylamino)-3-methylbutanoic acid
2-(2-fluorophenylamino)-3-methylbutanoic acid
2-(2-chlorophenylamino)-3-methylbutanoic acid
2-(3,4-dichlorophenylamino)-3-methylbutanoic acid
2-(2-chloro-4-cyanophenylamino)-3-methylbutanoic acid
2-(4-chloro-2,6-difluorophenylamino)-3-methylbutanoic acid
2-(2,4,6-trifluorophenylamino)-3-methylbutanoic acid
2-(4-ethoxyphenylamino)-3-methylbutanoic acid
2-(3-fluoro-4-trifluoromethylphenylamino)-3-methylbutanoic acid

| | |
|---|---|
| cyano(6-phenoxy-2-pyridyl)methyl | 2-(4-methyl-phenylamino)-3-methylbutanoate |
| cyano(6-phenoxy-2-pyridyl)methyl | 2-(4-chloro-phenylamino)-3-methylbutanoate |
| cyano(6-phenoxy-2-pyridyl)methyl | 2-(4-methoxy-phenylamino)-3-methylbutanoate |
| cyano(6-phenoxy-2-pyridyl)methyl | 2-(4-bromo-phenylamino)-3-methylbutanoate |
| cyano(6-phenoxy-2-pyridyl)methyl | 2-(4-t-butyl-phenylamino)-3-methylbutanoate |
| cyano(6-phenoxy-2-pyridyl)methyl | 2(4-ethyl-phenylamino)-3-methylbutanoate |
| cyano(6-phenoxy-2-pyridyl)methyl | 2-phenylamino-3-methylbutanoate |
| cyano(6-phenoxy-2-pyridyl)methyl | 2-(4-methylthiophenylamino)-3-methylbutanoate |
| cyano(6-phenoxy-2-pyridyl)methyl | 2-(4-cyclopropyl-phenylamino)-3-methylbutanoate |
| cyano(6-phenoxy-2-pyridyl)methyl | 2-(4-isopropyl-phenylamino)-3-methylbutanoate |
| cyano(6-phenoxy-2-pyridyl)methyl | 2-(3-fluoro-phenylamino)-3-methylbutanoate |
| cyano(6-phenoxy-2-pyridyl)methyl | 2-(2-methyl-phenylamino)-3-methylbutanoate |
| cyano(6-phenoxy-2-pyridyl)methyl | 2-(2-fluoro-phenylamino)-3-methylbutanoate |
| cyano(6-phenoxy-2-pyridyl)methyl | 2-(2-chloro-phenylamino)-3-methylbutanoate |
| cyano(6-phenoxy-2-pyridyl)methyl | 2-(3,4-dichloro-phenylamino)-3-methylbutanoate |
| cyano(6-phenoxy-2-pyridyl)methyl | 2-(2-chloro-4-cyanophenylamino)-3-methylbutanoate |
| cyano(6-phenoxy-2-pyridyl)methyl | 2-(4-chloro-2,6-difluorophenylamino)-3-methylbutanoate |
| cyano(6-phenoxy-2-pyridyl)methyl | 2-(2,4,6-trifluoro-phenylamino)-3-methylbutanoate |
| cyano(6-phenoxy-2-pyridyl)methyl | 2-(4-ethoxy-phenylamino)-3-methylbutanoate |
| cyano(6-phenoxy-2-pyridyl)methyl | 2-(3-fluoro-4-trifluoromethylphenylamino)-3-methylbutanoate |

EXAMPLE 7

The acid chloride of 2-(2-chloro-4-trifluoromethylphenylamino)-3-methylbutanoic acid is reacted with cyano[6-(3-fluorophenoxy)-2-pyridyl]methanol in ether as in Example 2 to give cyano[6-(3-fluorophenoxy)-2-pyridyl]methyl 2-(2-chloro-4-trifluoromethylphenylamino)-3-methylbutanoate.

By the above procedure, each of cyano[6-(4-fluorophenoxy)-2-pyridyl]methyl 2-(2-chloro-4-trifluoromethylphenylamino)-3-methylbutanoate, cyano[6-(4-methylphenoxy)-2-pyridyl]methyl 2-(2-chloro-4-trifluoromethylphenylamino)-3-methylbutanoate, cyano[6-(4-methoxyphenoxy)-2-pyridyl]methyl 2-(2-chloro-4-trifluoromethylphenylamino)-3-methylbutanoate, cyano[6-(4-chlorophenoxy)-2-pyridyl]methyl 2-(2-chloro-4-trifluoromethylphenylamino)-3-methylbutanoate, cyano[6-(methylthiophenoxy)-2-pyridyl]methyl 2-(2-chloro-4-trifluoromethyl-phenylamino)-3-methylbutanoate, and cyano[6-(4-trifluoromethylphenoxy)-2-pyridyl)]methyl 2-(2-chloro-4-trifluoromethylphenylamino)-3-methylbutanoate is prepared by the reaction of the acid chloride of 2-(2-chloro-4-trifluoromethylphenylamino)-3-methylbutanoic acid with each of cyano[6-(4-fluorophenoxy)-2-pyridyl]methanol, cyano[6-(4-methylphenoxy)-2-pyridyl]methanol, cyano[6-(4-methoxyphenoxy)-2-pyridyl]methanol, cyano[6-(4-chlorophenoxy)-2-pyridyl]methanol, cyano[6-(4-methylthiophenoxy)-2-pyridyl]methanol and cyano[6-(4-trifluoromethylphenoxy)-2-pyridyl]methanol, respectively.

EXAMPLE 8

The acid chloride of 2-(2-chloro-4-trifluoromethylphenylamino)-3-methylbutanoic acid is reacted with [6-(4-fluorophenoxy)-2-pyridyl]methanol using the procedure of Example 1 to give [6-(4-fluorophenoxy)-2-pyridyl]methyl 2-(2-chloro-4-trifluoromethylphenylamino)-3-methylbutanoate.

EXAMPLE 9

The alcohol, cyano[6-(3,4-dimethylphenoxy)-2-pyridyl]methanol and cyano[6-(2-fluorophenoxy)-2-pyridyl]methanol, is reacted with the acid chloride of 2-(2-chloro-4-trifluoromethylphenylamino)-3-methylbutanoic acid to yield cyano[6-(3,4-dimethylphenoxy)-2-pyridyl]methyl 2-(2-chloro-4-trifluoromethylphenylamino)-3-methylbutanoate and cyano[6-(2-fluorophenoxy)-2-pyridyl]methyl 2-(2-chloro-4-trifluoromethylphenylamino)-3-methylbutanoate.

EXAMPLE 10

To a mixture of (6-phenoxy-2-pyridyl)methyl 2-phenylamino-3-methylbutanoate (0.22 g), hexamethylphosphorictriamide (1 ml) and tetrahydrofuran (1 ml) is added methyl iodide (0.12 ml) and potassium carbonate (0.09 g). The reaction mixture is heated at about 55° over the weekend. The reaction is then poured into ice water and extracted with ether. The combined organic phases are washed with water and brine, dried over calcium sulfate and solvent evaporated to give (6-phenoxy-2-pyridyl)methyl 2-methyl-amino-2-phenylamino-3-methylbutanoate.

EXAMPLE 11

To a mixture of 2-(2-chloro-4-trifluoromethylphenylamino)-3-methylbutanoic acid (2.63 mmol), cold methylene chloride (5 ml) and dimethylaminopyridine (0.21 mmol) is added, at 0°, α-methyl(6-phenoxy-2-pyridyl)methanol (2.79 mmol) in 2 ml of methylene chloride and then dicyclohexylcarbodiimide (2.61 mmol). The reaction mixture is stirred at RT for about 4 hours and then worked up as in Example 3. The crude product is chromatographed on thin layer chromatography plates eluting with 30% ether/hexane to yield α-methyl(6-phenoxy-2-pyridyl)methyl 2-(2-chloro-4-trifluoromethylphenylamino)-3-methylbutanoate, MS m/e 492 (M+).

The alcohol, α-methyl(6-phenoxy-2-pyridyl) methanol is prepared by Grignard reaction of 6-phenoxypyridyl-2-carboxaldehyde and methylmagnesium bromide in tetrahydrofuran. 6-Phenoxypyridyl-2-carboxaldehyde is obtained by oxidation of 6-phenoxy-2-pyridylmethanol using chromium trioxide and pyridine in methylene chloride.

Using the procedure of this Example, 2-(2-chloro-4-trifluoromethylphenylamino)-3-methylbutanoic acid is reacted with α-methyl[6-(4-fluorophenoxy)-2-pyridyl]methanol to yield α-methyl[6-(4-fluorophenoxy)-2-pyridyl]methyl 2-(2-chloro-4-trifluoromethylphenylamino)-3-methylbutanoate. Similarly, 2-(2-fluoro-4-trifluoromethylphenylamino)-3-methylbutanoic acid is reacted with α-methyl(6-phenoxy-2-pyridyl)methanol to yield α-methyl(6-phenoxy-2- pyridyl)methyl 2-(2-fluoro-4-trifluoromethylphenylamino)-3-methylbutanoate, MS m/e 476 (M+).

EXAMPLE 12

Following the procedure of Example 11, 2-(2-chloro-4-trifluoromethylphenylamino)-3-methylbutanoic acid is reacted with α-ethynyl(6-phenoxy-2-pyridyl)methanol to yield the ester, α-ethynyl(6-phenoxy-2-pyridyl)methyl 2-(2-chloro-4-trifluoromethylphenylamino)-3-methylbutanoate, MS m/e 502 (M+).

The foregoing alcohol is prepared by Grignard reaction of 6-phenoxypyridyl-2-carboxaldehyde and ethynyl magnesium bromide in tetrahydrofuran.

EXAMPLE 13

To 2-(2-chloro-4-trifluoromethylphenylamine)-3-methyl-butanoic acid (0.29 g) in 10 ml of benzene is added 0.21 g of oxalyl chloride and dimethylformanide at RT. After about 5 minutes, the solution is warmed to about 40°, stripped of solvent and excess oxalyl chloride. Then to the acid chloride in tetrahydrofuran is added (6-phenoxy-2-pyridyl)methylthiol (0.2 g) and dimethylaminopyridine (0.22 g) with stirring. The reaction mixture is stirred for about 18 hours and then worked up in ether, washing with water and brine, and drying over sodium sulfate. The reaction product is chromatographed on plates using 20% ethyl acetate (hexane to yield S-(6-phenoxy-2-pyridyl)methyl thiolester of 2-(2-chloro-4-trifluoromethylphenylamino)-3-methylbutanoic acid, MS m/e 494 (M+), (A; R is oxygen, $R^1$ is 2-chloro-4-trifluoromethylphenyl, $R^2=R^4=R^5$ is hydrogen, $R^3$ is isopropyl).

The thiol, (6-phenoxy-2-pyridyl)methylthiol, is prepared by the reaction of (6-phenoxy-2-pyridyl)methyl bromide with thioacetic acid using sodium hydride to form the thiolester which is then converted to the desired thiol using lithium aluminum hydride.

EXAMPLE 14

Using the procedure of Example 11, α-ethyl(6-phenoxy-2-pyridyl)methanol is reacted with 2-(2-chloro-4-trifluoromethylphenylamino)-3-methylbutanoic acid to yield α-ethyl(6-phenoxy-2-pyridyl)methyl 2-(2-chloro-4-trifluoromethylphenylamino)-3-methylbutanoate, MS m/e 506 (M+).

EXAMPLE 15

Using the procedure of Example 1, the acid chloride of 2-(2-chloro-4-trifluoromethylphenylamino)-3-methylbutanoic acid is reacted with (6-benzoyl-2-pyridyl)methanol to yield (6-benzoyl-2-pyridyl)methyl 2-(2-chloro-4-trifluoromethylphenylamino)-3-methylbutanoate, MS m/e 490 (M+).

Using the procedure of Example 11, (6-phenylthio-2-pyridyl)methanol is reacted with 2-(2-chloro-4-trifluoromethylphenylamino)-3-methylbutanoic acid to yield (6-phenylthio-2-pyridyl)methyl 2-(2-chloro-4-trifluoromethylphenylamino)-3-methylbutanoate, MS m/e 494 (M+).

(6-Phenoxy-2-pyridyl)methyl 2-(2-fluoro-4-trifluoromethylphenylamino)-3-methylbutanoate, MS m/e 462 (M+) is prepared using the procedure of Example 1 from (6-phenoxy-2-pyridyl)methanol and the acid chloride of 2-(2-fluoro-4-trifluoromethylphenylamino)-3-methylbutanoic acid.

EXAMPLE 16

A. To a cooled solution, about 5°, of 2-(2-chloro-4-trifluoromethylphenylamino)-3-methylbutanoic acid (3.38 mmol) in 25 ml of dimethylformamide is added triethylamine (3.38 mmol) and ethyl chloroformate (3.38 mmol). The reaction mixture is stirred for about 15 minutes and then sodium hydrosulfide (6.76 mmol) and 10 ml of dimethylformamide are added. The mixture is stirred at 5° for about 1.5 hours. The reaction is worked up by adding ether and then acidifying with 5% $H_2SO_4$. The ether layer is washed with water and brine, dried over sodium sulfate and solvent evaporated to give the thioacid of 2-(2-chloro-4-trifluoromethylphenylamino)-3-methylbutanoic acid.

B. To 15 ml of dimethylformamide and 10 ml of tetrahydrofuran is added 1.60 mmol of the thioacid of part A, $KHCO_3$ (4.01 mmol) and the mesylate of α-cyano-(6phenoxy-2-pyridyl)methanol (1.60 mmol). The reaction mixture is stirred at RT for about 18 hours. The mixture is taken up in ether, washed with water and brine, dried over sodium sulfate and solvent stripped to give S-α-cyano-(6-phenoxy-2-pyridyl)methyl thioester of 2-(2-chloro-4-trifluoromethylphenylamino)-3-methylbutanoic acid.

EXAMPLE 17

Following the procedure of Example 1, the acid chloride of each of 2-(4-chlorophenylamino)-3-methylbutanoic acid and 2-(2-fluoro-4-trifluoromethylphenylamino)-3-methylbutanoic acid is reacted with (6-benzoyl-2-pyridyl)methanol to yield (6-benzoyl2-pyridyl)methyl 2-(4-chlorophenylamino)-3-methylbutanoate and (6-benzoyl-2-pyridyl)methyl 2-(2-fluoro-4-trifluoromethylphenylamino)-3-methylbutanoate.

To 15 g of 6-methyl-2-pyridylcarboxylic acid (122 mmol) in 200 ml benzene is added dropwise 19.1 g (150 mmol) oxalyl chloride (dissolved in 30 ml benzene) with ice bath cooling. The solution is allowed to come to RT and is stirred 1 hour, after which it is stripped, 100 ml of benzene is added, and it is stripped again. The residue is taken up in 200 ml benzene and 41 g of aluminumtrichloride (310 mmol) is added in portions over a 3 hour period with ice bath cooling. The solution is heated to 25° for 1 hour, then heated to reflux for 2 hours, and finally cooled and stirred overnight. The mixture is poured onto ice/conc. HCl, then washed with ether. Fifty Percent (50%) sodium hydroxide is added until the precipitate is dissolved. The solution is extracted with CHCl₃, washed with water, dried and stripped, leaving 6-benzoyl-2-methylpyridine.

The 6-benzoyl-2-methylpyridine (3.9 g, 21 mmol), in 20 ml CHCl₃, is added over 1 hour to 4.2 g (21 mmol) m-chloroperbenzoic acid (in 50 ml CHCl₃). The temperature is kept below 25° as the mixture is stirred overnight. The reaction is diluted with CHCl₃, washed with sat. NaHSO₃, water, 20% NaHCO₃ (2×) and then water, dried, stripped and finally titrated with hexane/ethyl acetate to give 6-benzoyl-2-methylpyridine N-oxide.

Acetic anhydride (6.6 ml) is heated to 115°, after which 6-benzoyl-2-methylpyridine N-oxide is added in portions over 1 hour. The mixture is then held at 115° for 1 hour after the addition. The reaction is poured onto ice and extracted with ether (3×). The combined ether phases are washed with sat. NaHCO₃ (2×) and water until neutral, dried and stripped. The product is preparatory thin layer chromatographed, the least polar band giving 2-(acetoxymethyl)-6-benzoylpyridine.

Potassium hydroxide (1.1 g, 18 mmol) is dissolved in 25 ml methanol, after which is added 2-(acetoxymethyl)-6-benzoylpyridine (2.3 g, 9 mmol) in 20 ml methanol and the mixture is then stirred overnight. The mixture is diluted with water and saturated sodium chloride, then extracted with ether (2×), washed with sat. sodium chloride, dried over magnesium sulfate and stripped to yield (6-benzoyl-2-pyridyl)methanol.

EXAMPLE 18

A mixture of (6-benzoyl-2-pyridyl)methanol (1.5 g, 7 mmol), potassium hydroxide (1.3 g, 23 mmol) and hydrazine 85% (1 ml, 25 mmol) in triethylene glycol (10 ml) is refluxed for 1½ hours, and then the water and excess hydrazine are removed by a takeoff condenser until the temperature rises to 195°–200°. After 4 hours at 195°–200°, the solution is cooled, poured into ice and water (50 ml) and extracted with ether 3× 20 ml). The combined ether layers are washed with water 3× 20 ml), brine (10 ml) and dried over calcium sulfate. Removal of solvents gives (6-benzyl-2-pyridyl)methanol.

Following the procedure of Example 1, the acid chloride of each of 2-(4-chlorophenylamino)-3-methylbutanoic acid, 2-(2-chloro-4-trifluoromethylphenylamino)-3-methylbutanoic acid and 2-(2-fluoro-4-trifluoromethylphenylamino)-3-methylbutanoic acid is reacted with (6-benzyl-2-pyridylmethanol to yield (6-benzyl-2-pyridyl)methyl 2-(4-chlorophenylamino)-3-methylbutanoate, (6-benzyl-2-pyridyl)methyl 2-(2-chloro-4-trifluoromethylphenylamino)-3-methylbutanoate, and (6-benzyl-2-pyridyl)methyl 2-(2-fluoro-4-trifluoromethylphenylamino)-3-methylbutanoate.

Two groups of 10 each of 0–24 hour III instar Heliothis virescens lavae were treated with 1 μl of the compound, (6-phenoxy-2-pyridyl)methyl 2-(2-chloro-4-trifluoromethylphenoxy-2-pyridyl)methyl 2-(2-chloro-4-trifluoromethylphenylamino)-3-methylbutanoate, in acetone at five different concentrations by application to the dorsum of the thorax. Two groups of 10 each are treated identically with 1 μl acetone only as controls. Larvae are held individually in 30 ml plastic cups provided with artificial medium for 72 hours at 25° and 16 hr photoperiod. After 72 hr the number of dead is calculated as a percentage of the total number originally treated and then corrected for any mortality in the control groups using Abbott's formula. The $LD_{50}$ of the compound was less than 0.05%.

What is claimed is:

1. A compound of the formula:

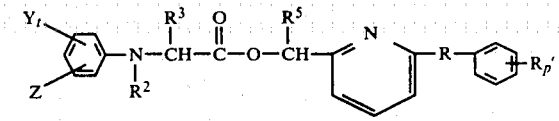

wherein,
R is oxygen, sulfur, methylene or carbonyl;
R' is fluoro, bromo, chloro, trifluoromethyl, methyl, methoxy or methylthio;
p is zero, one or two; W is oxygen or sulfur;
t is zero, one, two, three or four; Y is independently selected from hydrogen, lower alkyl, lower haloalkyl, lower alkoxy, lower alkylthio, lower alkylcarbonyl, lower alkoxycarbonyl, lower acyloxy, halogen, cyano, nitro, and lower haloalkylthio; and Z is independently selected from the values of Y, cycloalkyl having 3 to 8 carbon atoms, and lower haloalkoxy; or Y and Z form a methylenedioxy group;
$R^2$ is hydrogen or lower alkyl;
$R^3$ is lower alkyl of 2 to 5 carbon atoms, lower alkenyl of 2 to 5 carbon atoms, lower haloalkyl of 1 to 4 carbon atoms, lower haloalkenyl of 2 to 4 carbon atoms, or lower cycloalkyl of 3 or 4 carbon atoms;
$R^4$ is hydrogen or fluoro;
$R^5$ is hydrogen, cyano, ethynyl, methyl, ethyl or trifluoromethyl; and the salt thereof of a strong inorganic acid or organic acid.

2. The compound, the (6-phenoxy-2-pyridyl)methyl ester of N-(2-chloro-4-trifluoromethylphenyl)valine, according to claim 1.

3. The compound, S-(6-phenoxy-2-pyridyl)methyl thiolester of 2-(2-chloro-4-trifluoromethylphenylamino)-3-methylbutanoic acid, according to claim 1.

4. The compound, [6-(4-fluorophenoxy)-2-pyridyl]methyl 2-(2-chloro-4-trifluoromethylphenylamino)-3-methylbutanoate, according to claim 1.

5. The compound, α-methyl(6-phenoxy-2-pyridyl)methyl 2-(2-chloro-4-trifluoromethylphenylamino)-3-methylbutanoate, according to claim 1.

6. The compound, (6-phenoxy-2-pyridyl)methyl 2-(2-fluoro-4-trifluoromethylphenylamino)-3-methylbutanoate, according to claim 1.

7. The compound, α-methyl(6-phenoxy-2-pyridyl)methyl 2-(2-fluoro-4-trifluoromethylphenylamino)-3-methylbutanoate, according to claim 1.

8. A compound according to claim 1 of the formula:

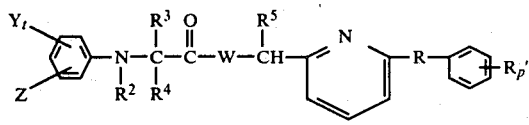

9. A compound according to claim 8 wherein $R^2$ is hydrogen or methyl.

10. A compound according to claim 9 wherein $R^5$ is hydrogen, cyano, ethynyl or methyl.

11. A compound according to claim 10 wherein R' is hydrogen, methyl, fluoro, chloro, methoxy, methylthio or trifluoromethyl.

12. A compound according to claim 11 wherein p is zero or one and $R^3$ is isopropyl.

13. A compound according to claim 12 wherein R is oxygen.

14. A compound according to claim 13 wherein Y is hydrogen, bromo, chloro, fluoro, lower alkyl of 1 to 4 carbon atoms, trifluoromethyl, lower alkoxy of 1 to 2 carbon atoms, lower alkylthio of 1 to 2 carbon atoms, or cyano and Z is hydrogen, cyclopropyl or independently selected from the values of Y.

15. A compound according to claim 14 wherein Z is hydrogen.

16. A compound according to claim 15 wherein t is one, two or three.

17. A compound according to claim 16 wherein $R^2$ is hydrogen and p is zero.

18. A compound according to claim 16 wherein t is one.

19. A compound according to claim 18 wherein $R^5$ is hydrogen, cyano or methyl.

20. A compound according to claim 19 wherein $R^2$ is hydrogen and p is zero.

21. A compound according to claim 14 wherein t is one, Y is in the ortho position and Z is in the para position.

22. A compound according to claim 21 wherein $R^5$ is hydrogen, cyano or methyl.

23. A compound according to claim 22 wherein $R^2$ is hydrogen and p is zero.

24. A compound according to claim 23 wherein Y is hydrogen, methyl, chloro or fluoro.

25. A compound according to claim 24 wherein Z is hydrogen, methyl, chloro, fluoro, bromo or trifluoromethyl.

26. A compound according to claim 19 wherein $R^5$ is methyl, p is zero or one, R' is fluoro, and $R^2$ is hydrogen.

27. A compound according to claim 26 wherein p is zero.

28. A compound according to claim 22, wherein Y is chloro or fluoro, Z is trifluoromethyl, $R^5$ is methyl, $R^2$ is hydrogen and R' is fluoro.

29. A compound according to claim 28 wherein p is zero.

30. A method for the control of pests selected from insects of the order Lepidoptera, Orthoptera, Heteroptera, Homoptera, Diptera, Coleoptera and Hymenoptera; mites of the family Tetranychidae and Tarsonemidae and ticks of the family Ornithodoros which comprises applying to the locus of the pest a compound according to claim 1, in a pesticidally effective amount, in a suitable liquid or solid carrier.

31. The method of claim 30 wherein the pest is an insect and the compound is a compound according to claim 20.

32. The method according to claim 31 wherein the insect is a member of the order Lepidoptera.

* * * * *